(12) United States Patent
Denney et al.

(10) Patent No.: US 9,370,516 B2
(45) Date of Patent: Jun. 21, 2016

(54) USE OF GHRELIN RECEPTOR INVERSE AGONISTS OR ANTAGONISTS FOR TREATING SLEEP DISORDERS

(71) Applicant: Pfizer Inc., New York, NY (US)

(72) Inventors: William S. Denney, Somerville, MA (US); Margaret Jackson, Somerville, MA (US); Gabriele Sonnenberg, Cambridge, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/398,800

(22) PCT Filed: May 21, 2013

(86) PCT No.: PCT/IB2013/054177
§ 371 (c)(1),
(2) Date: Nov. 4, 2014

(87) PCT Pub. No.: WO2013/182933
PCT Pub. Date: Dec. 12, 2013

(65) Prior Publication Data
US 2015/0119381 A1    Apr. 30, 2015

Related U.S. Application Data

(60) Provisional application No. 61/812,416, filed on Apr. 16, 2013, provisional application No. 61/655,177, filed on Jun. 4, 2012.

(51) Int. Cl.
*A61K 31/506* (2006.01)
*A61K 31/397* (2006.01)

(52) U.S. Cl.
CPC ............ *A61K 31/506* (2013.01); *A61K 31/397* (2013.01)

(58) Field of Classification Search
CPC .......................... A61K 31/397; A61K 31/506
See application file for complete search history.

(56) References Cited

U.S. PATENT DOCUMENTS

2005/0171131 A1    8/2005    Kosogof et al.
2011/0230461 A1    9/2011    Bhattacharya

FOREIGN PATENT DOCUMENTS

WO    2008/008286    1/2008

OTHER PUBLICATIONS

Bray et al., "The Prader-Willie Syndrome: A study of 40 Patients and a Review of the Literature," Medicine, Mar. 1983, vol. 62, Issue 2, pp. 59-80.*
Abizaid, et al., "Ghrelin modulates the activity and synaptic input organization of midbrain dopamine neurons while promoting appetite", The Journal of Clinical Investigation, vol. 116(12), pp. 3229-3239 (2006).
Goldstone, "Prader-Willi syndrome: advances in genetics, pathophysiology and treatment", TRENDS in Endocrinology and Metabolism, vol. 15(1), pp. 12-20 (2004).
Orr, et al., "One-pot synthesis of chiral azetidines from chloroaldehyde and chiral amines", Tetrahedron Letters, vol. 52(28), pp. 3618-3620 (2011).
Fernando, et al., "Spiroazetidine-piperidine bromoindane as a key modular template to access a variety of compounds via C—C and C—N bond-forming reactions", Tetrahedron Letters, vol. 53(47), pp. 6351-6354 (2012).

* cited by examiner

*Primary Examiner* — Sreeni Padmanabhan
*Assistant Examiner* — Jody Karol
(74) *Attorney, Agent, or Firm* — Mary J. Hosley (57) ABSTRACT

The present invention relates to methods of treating sleep disorders in patients comprising administration of a ghrelin receptor inverse agonist or antagonist. The invention also includes methods of treating sleep disorders comprising the administration of a pharmaceutical composition comprising a ghrelin receptor inverse agonist or antagonist and at least one pharmaceutically acceptable carrier, diluent, or excipient.

4 Claims, 5 Drawing Sheets

| Study | Dose (mg) | Subjects (n/N) |
|---|---|---|
| B3301001 | 0 | 0/35 |
| | 2 | 0/6 |
| | 10 | 0/6 |
| | 50 | 3/6 |
| | 100 | 0/6 |
| | 100 fed | 7/9 |
| | 150 | 5/8 |
| | 300 | 9/12 |
| | 40 divided, fed | 0/6 |
| | 300 divided, fed | 1/6 |

| Study | Dose (mg) | Subjects (n/N) |
|---|---|---|
| B3301002 | 0 | 3/12 |
| | 2 BID | 0/6 |
| | 10 BID | 0/6 |
| | 40 BID | 1/5 |
| | 100 BID | 5/5 |

| Study | Dose (mg) | Subjects (n/N) |
|---|---|---|
| B3301007 | 100 (IR) | 4/16 |
| | 100 (EPOC 6 hr) | 3/15 |
| | 100 (EPOC 6 hr), fed | 0/8 |
| | 100 (EPOC 14 hr) | 2/15 |
| | 100 (EPOC 14 hr), fed | 0/7 |

USE OF GHRELIN RECEPTOR INVERSE AGONISTS OR ANTAGONISTS FOR TREATING SLEEP DISORDERS

FIELD OF THE INVENTION

The present invention relates to compounds that are ghrelin receptor inverse agonists/antagonists useful for treating sleep disorders. The invention also relates to pharmaceutical compositions containing such compounds.

BACKGROUND

Insomnia, the most common sleep disorder, affects approximately 50-70 million American adults. It is characterized by difficulty falling asleep, waking frequently during the night, waking too early and not being able to return to sleep, or waking up and not feeling refreshed.

Early treatments for insomnia commonly employed central nervous system (CNS) depressants such as barbiturates. These compounds typically have long half lives and have a well-known spectrum of side effects, including lethargy, confusion, depression and next day hangover effects. In addition, chronic use has been associated with a high potential for addiction involving both physical and psychological dependence. Treatments moved away from barbiturates and other CNS depressants toward the benzodiazepine class of sedative-hypnotic agents. This class of compounds produces a calming effect that results in a sleep-like state in patients and animals, with a greater safety margin than prior hypnotics. However, many benzodiazepines possess side effects that limit their usefulness in certain patient populations. These problems include synergy with other CNS depressants (especially alcohol), the development of tolerance upon repeat dosing, rebound insomnia following discontinuation of dosing, hangover effects the next day and impairment of psychomotor performance and memory. More recent treatments for insomnia have used non-benzodiazepine compounds. Ambien (zolpidem), Sonata (zaleplon) are examples of approved drug products. A need exists in the art for safe and therapeutically effective non-benzodiazepine agents for treating sleep disorders.

Night Eating Syndrome (NES) is generally associated with insufficient food intake in the first half of the day, evening hyperphagia and then insomnia and also sleep awakenings. See, e.g., Vander Wal, Jillon S., Clinical Psychology Review (2012) 32(1), 49-59. Despite increased awareness of NES, it is still not recognized, and more importantly, approaches to treatment continue to be investigated without success.

The present invention relates to the use of ghrelin receptor inverse agonists or antagonists for treating sleep disorders.

SUMMARY OF THE INVENTION

The present invention relates to methods of treating sleep disorders in patients comprising administering to the patient, in need of such treatment, a therapeutically effective amount of a ghrelin receptor inverse agonist or antagonist.

In another embodiment, the present invention relates to methods of treating sleep disorders in patients comprising administering to the patient, in need of such treatment, a pharmaceutical composition comprising a therapeutically effective amount of a ghrelin receptor inverse agonist or antagonist and at least one pharmaceutically acceptable carrier, diluent, or excipient.

DETAILED DESCRIPTION OF THE INVENTION

In another embodiment, the present invention relates to methods of treating primary insomnia in patients comprising administering to the patient, in need of such treatment, a therapeutically effective amount of a ghrelin receptor inverse agonist or antagonist.

In another embodiment, the present invention relates to methods of treating excessive daytime sleepiness in patients comprising administering to the patient, in need of such treatment, a therapeutically effective amount of a ghrelin receptor inverse agonist or antagonist. The methods of present invention include treating excessive daytime sleepiness in patients diagnosed with Prader-Willi syndrome.

In another embodiment, the present invention relates to methods of treating NES in patients comprising administering to the patient, in need of such treatment, a therapeutically effective amount of a ghrelin receptor inverse agonist or antagonist.

In another embodiment, the present invention relates to methods of treating primary insomnia in patients comprising administering to the patient, in need of such treatment, a pharmaceutical composition comprising a therapeutically effective amount of a ghrelin receptor inverse agonist or antagonist and at least one pharmaceutically acceptable carrier, diluent, or excipient.

In another embodiment, the present invention relates to methods of treating excessive daytime sleepiness in patients comprising administering to the patient, in need of such treatment, a pharmaceutical composition comprising a therapeutically effective amount of a ghrelin receptor inverse agonist or antagonist and at least one pharmaceutically acceptable carrier, diluent, or excipient. The methods of present invention include treating excessive daytime sleepiness in patients diagnosed with Prader-Willi syndrome.

In another embodiment, the present invention relates to methods of treating NES in patients comprising administering to the patient, in need of such treatment, a pharmaceutical composition comprising a therapeutically effective amount of a ghrelin receptor inverse agonist or antagonist and at least one pharmaceutically acceptable carrier, diluent, or excipient.

In another embodiment, the present invention relates to a method of treating sleep disorders in patients comprising administering to the patient, in need of such treatment, a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl) ethanone, or a pharmaceutically acceptable salt thereof.

In another embodiment, the present invention relates to a method of treating primary insomnia in patients comprising administering to the patient, in need of such treatment, a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone, or a pharmaceutically acceptable salt thereof.

In another embodiment, the present invention relates to a method of treating excessive daytime sleepiness in patients comprising administering to the patient, in need of such treatment, a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone, or a pharmaceutically acceptable salt thereof. The methods of present invention are useful for treating excessive daytime sleepiness in patients diagnosed with Prader-Willi syndrome.

In another embodiment, the present invention relates to methods of treating NES in patients comprising administering to the patient, in need of such treatment, a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone, or a pharmaceutically acceptable salt thereof.

In another embodiment, the present invention relates to methods of treating sleep disorders in patients comprising administering to the patient, in need of such treatment, a pharmaceutical composition comprising a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone, or a pharmaceutically acceptable salt thereof, and at least one pharmaceutically acceptable carrier, diluent, or excipient.

In another embodiment, the present invention relates to methods of treating primary insomnia in patients comprising administering to the patient, in need of such treatment, a pharmaceutical composition comprising a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone, or a pharmaceutically acceptable salt thereof, and at least one pharmaceutically acceptable carrier, diluent, or excipient.

In another embodiment, the present invention relates to methods of treating excessive daytime sleepiness in patients comprising administering to the patient, in need of such treatment, a pharmaceutical composition comprising a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone, or a pharmaceutically acceptable salt thereof, and at least one pharmaceutically acceptable carrier, diluent, or excipient. The methods of present invention are useful for treating excessive daytime sleepiness in patients diagnosed with Prader-Willi syndrome.

In another embodiment, the present invention relates to methods of treating NES in patients comprising administering to the patient, in need of such treatment, a pharmaceutical composition comprising a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone, or a pharmaceutically acceptable salt thereof, and at least one pharmaceutically acceptable carrier, diluent, or excipient.

In another embodiment, the present invention also provides:

the use of a ghrelin receptor inverse agonist or antagonist as described herein, for the manufacture of a medicament for treating a sleep disorder, particularly primary insomnia, excessive daytime sleepiness or NES;

a ghrelin receptor inverse agonist or antagonist as described herein for use as a medicament;

a ghrelin receptor inverse agonist or antagonist as described herein for use in the treatment of a sleep disorder, particularly primary insomnia, excessive daytime sleepiness or NES;

a pharmaceutical composition comprising a ghrelin receptor inverse agonist or antagonist as described herein and a pharmaceutically acceptable excipient; and a pharmaceutical composition for treatment of a sleep disorder, particularly primary insomnia, excessive daytime sleepiness or NES, comprising a ghrelin receptor inverse agonist or antagonist as described herein;

particularly where the ghrelin receptor inverse agonist or antagonist may be (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone or a pharmaceutically acceptable salt thereof.

(R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone or a pharmaceutically acceptable salt thereof may simply be generally referenced herein as Example 1.

In another embodiment, the present invention also provides any method discussed herein where the ghrelin receptor inverse agonist or antagonist, particularly R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone or a pharmaceutically acceptable salt thereof, is administered in combination with another pharmacologically active agent.

In another embodiment, the ghrelin receptor inverse agonist or antagonist, particularly Example 1, may be employed in combination with other pharmacologically active agents, also referred to as compounds, which are known in the art, either administered separately or in the same pharmaceutical compositions, include, but are not limited to: insulin sensitizers including (i) PPAR.gamma. antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH.sub.2); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) .alpha.-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor.alpha. agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPAR.alpha. agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPAR.alpha. agonists as described in WO 97/36579 by Glaxo; (g) PPAR.delta. agonists; (h) PPAR.alpha./.delta. agonists, such as muraglitazar, and the compounds disclosed in U.S. Pat. No. 6,414,002; and (i) anti-obesity agents, such as (1) growth hormone secretagogues, growth hormone secretagogue receptor agonists/antagonists, such as NN703, hexarelin, MK-0677, SM-130686, CP-424, 391, L-692,429, and L-163,255; (2) protein tyrosine phosphatase-1B (PTP-1B) inhibitors; (3) cannabinoid receptor ligands, such as cannabinoid CB.sub.1 receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) .beta.3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate; (7) neuropeptide Y1 antagonists, such as BIBP3226, J-115814, BIBO 3304, LY-357897, CP-671906, GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065; (18) galanin antagonists; (19) CCK agonists; (20) CCK-A (cholecystokinin-A) agonists, such as AR-R 15849, GI 181771, JMV-180, A-71378, A-71623 and SR14613; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) .beta.-hydroxy steroid dehydrogenase-1 inhibitors (.beta.-HSD-1); 26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) a second or third ghrelin receptor inverse agonst or antagonist; (30) leptin, including recombinant patient leptin (PEG-OB, Hoffman La Roche) and recombinant methionyl patient leptin (Amgen); (31) leptin derivatives; (32) BRS3 (bombesin receptor subtype 3) agonists such as [D-Phe6,beta-Ala11,Phe13, Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (GlaxoSmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TT-NPB), retinoic acid; (37) thyroid hormone.beta. agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, MK-431, P93/01, TSL 225, TMC-2A/2B/2C, FE 999011, P9310/K364, VIP 0177, SDZ 274-444; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11.beta. HSD-1 (11-beta hydroxy steroid dehydrogenase type 1) inhibitor such as BVT 3498, BVT 2733; (58) a minorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide.

The term "pharmaceutically acceptable salt" as used herein means those salts which are, within the scope of sound medical judgement, suitable for use in contact with the tissues of patients and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in Berge et al., *J. Pharmaceutical Sciences,* 1977, 66: 1-19. The salts can be prepared in situ during the final isolation and purification of Example 1 of the present invention or separately by reacting the free base of Example 1 with a suitable organic or inorganic acid. Representative acid addition salts include, but are not limited to acetate, adipate, alginate, citrate, aspartate, benzoate, benzenesulfonate, bicarbonate, bisulfate, butyrate, camphorate, camphorsufonate, citrate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, phosphate, picrate, pivalate, propionate, succinate, sulphate, tartrate, thiocyanate, and p-toluenesulfonate.

The term "ghrelin receptor" as used herein means a G protein-coupled receptor, known as the growth hormone secretagogue receptor (GHSR1a or GHS-1aR).

The term "sleep disorders" as used herein includes approximately 70 syndromes characterized by disturbance in the patient's amount of sleep, quality or timing of sleep, or in behaviors or physiological conditions associated with sleep. Representative examples of sleep disorder syndromes include, but are not limited to, insomnia, primary insomnia, sleep apnea, narcolepsy, restless leg syndrome, circadian rhythm sleep disorder, REM sleep behavior disorder, somnambulism (sleepwalking), sleep bruxism (teeth grinding), hypersomnia, exploding head syndrome, sleep paralysis, and excessive daytime sleepiness (EDS).

EDS is one of the typical features of patients with Prader-Willi syndrome (PWS); caregivers describe PWS children as sleepy and with highly frequent daytime napping. EDS is demonstrated with reduced sleep onset latencies both at nightime and during the daytime on the multiple sleep latency test. Parental reports and questionnaires show the presence of EDS in 90-100% of adults with PWS. PWS patients also have higher self-reported levels of EDS, compared with other intellectual disability groups and non-PWS controls.

"NES has been characterized in terms of eating patterns, sleep disturbances, clinical course, and familial aggregation. In comparison to healthy controls, persons with NES consume a significantly greater proportion of their calories after the evening meal, wake more often during the night, and are more likely to eat upon awakening than controls." Vander Wal, supra, p 50, reference to an internal Table and citations omitted.

The term "patient" as used herein means a human.

The present invention also provides pharmaceutical compositions which comprise a ghrelin receptor inverse agonist or antagonist, particularly Example 1, formulated together with one or more non-toxic pharmaceutically acceptable carriers. The pharmaceutical compositions may be specially formulated for oral administration in solid or liquid form, for parenteral injection, or for rectal administration.

The term "pharmaceutically acceptable carrier" as used herein means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise a ghrelin receptor inverse agonist or antagonist, particularly Example 1, formulated together with one or more non-toxic pharmaceutically acceptable carriers. The pharmaceutical compositions can be formulated for oral administration in solid or liquid form, for parenteral injection or for rectal administration.

The pharmaceutical compositions of this invention can be administered to patients orally, parenterally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the ghrelin receptor inverse agonist or antagonist, particularly Example 1, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the ghrelin receptor inverse agonist or antagonist, particularly Example 1, of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The ghrelin receptor inverse agonist or antagonist, particularly Example 1, can also be in micro-encapsulated form, if appropriate, with one or more pharmaceutically acceptable carriers as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the ghrelin receptor inverse agonist or antagonist, particularly Example 1, can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the ghrelin receptor inverse agonist or antagonist, particularly Example 1, is mixed with at least one inert pharmaceutically acceptable carrier such as sodium citrate or calcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Liquid dosage forms for oral administration include pharmaceutically acceptable emulsions, microemulsions, solutions, suspensions, syrups and elixirs. In addition to the ghrelin receptor inverse agonist or antagonist, particularly Example 1, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Actual dosage levels of the ghrelin receptor inverse agonist or antagonist, particularly Example 1, in the pharmaceutical compositions of this invention can be varied so as to obtain an amount of the ghrelin receptor inverse agonist or antagonist, particularly Example 1, which is effective to achieve the desired therapeutic response for a particular patient, compositions, and mode of administration. The selected dosage level will depend upon the activity of the particular ghrelin receptor inverse agonist or antagonist, the route of administration, the severity of the condition being treated, and the condition and prior medical history of the patient being treated.

The total daily dose of the ghrelin receptor inverse agonist or antagonist, particularly Example 1, of this invention administered to a patient, from about 0.003 to about 10 mg/kg/day. For purposes of oral administration, more preferable doses can be in the range of from about 0.01 to about 5 mg/kg/day. Preferred doses range between 25 and 300 mgs per day. Most preferred is 75 to 200 mgs per day. If desired, the effective daily dose can be divided into multiple doses for purposes of administration, e.g. two to four separate doses per day.

All patents, patent applications, and literature references cited in the specification are herein incorporated by reference in their entirety.

(R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone may be prepared using the synthetic methodology disclosed herein or in US 2011/0230461.

Example 1

(R)-2-(2-methylimidazo[2,1-b]thiazol-6-yl)-1-(2-(5-
(6-methylpyrimidin-4-yl)-2,3-dihydro-1H-inden-1-
yl)-2,7-diazaspiro[3.5]nonan-7-yl)ethanone 2-(2-methylimidazo[2,1-b]thiazol-6-yl)acetic acid
hydrochloride

A solution of bromine (436 g, 2.73 mol) in acetic acid (750 mL) was added to a solution of ethyl 3-oxobutanoate (355 g, 2.73 mol) in acetic acid (1000 mL). The mixture was stirred at room temperature for 72 hours and was concentrated under reduced pressure at 45° C. to remove the acetic acid. The residue was partitioned between methylene chloride (400 mL) and water (250 mL). The organic layer was washed with saturated sodium bicarbonate (2×300 mL), water (300 mL), brine (125 mL) and was dried over anhydrous magnesium sulfate. The solution was filtered and concentrated to give ethyl 4-bromo-3-oxobutanoate as a yellow oil (421 g).

To a solution of 2-amino-5-methylthiazole (150 g, 1.31 mol) in acetone (1500 mL) was slowly added ethyl 4-bromo-3-oxobutanoate (345 g, 1.65 mol). The temperature of the reaction mixture was maintained between 22-40° C. The mixture turned into a thick paste and acetone (300 mL) was added to facilitate stirring. After stirring at room temperature overnight, the mixture was filtered and the filter cake was washed with acetone to provide a white solid. The solid was washed with hexanes and was dried in a vacuum oven at 40° C. for 4 hours to give 4-(2-amino-5-methyl-thiazol)-3-oxobutyric acid ethyl ester hydrobromide (272 g).

To 4-(2-amino-5-methyl-thiazol)-3-oxobutyric acid ethyl ester hydrobromide (272 g, 0.84 mol) was added anhydrous ethanol (675 mL) and the thick mixture was heated at 90° C. for 2 hours. During this time, the solids went into solution. The reaction mixture was concentrated to give a brown semi-solid which was triturated with ethanol to provide a white fluffy solid which was collected by filtration. The solids were washed with Et$_2$O and dried under vacuum at 40° C. for 4 hours to give ethyl (2-methylimidazo[2,1-b][1,3]thiazol-6-yl)acetate hydrobromide (226 g).

Ethyl (2-methylimidazo[2,1-b][1,3]thiazol-6-yl)acetate hydrobromide (226 g, 0.74 mol) was dissolved in water (350 mL) and the solution was adjusted to pH 7 by addition of potassium carbonate (51.0 g, 0.37 mol). The aqueous solution was extracted with methylene chloride (300 mL) and the organic phase was washed with brine (150 mL), dried over anhydrous magnesium sulfate, filtered and concentrated to give ethyl (2-methylimidazo[2,1-b][1,3]thiazol-6-yl)acetate as a brown oil (151.3 g).

Ethyl (2-methylimidazo[2,1-b][1,3]thiazol-6-yl)acetate (151.3 g, 0.67 mol) was dissolved in 10% aqueous HCl (435 mL) and the mixture was heated at reflux for 2 hours. The reaction mixture was cooled to room temperature and was concentrated in vacuo to give a yellow oil. Ethanol (100 mL) and diethylether (200 mL) were added and the resulting white precipitate was collected by filtration and dried in a vacuum oven overnight to give 144.3 g (93%) the title compound. MS (ES+) 197.1 (M+H)$^+$. $^1$H NMR (CD$_3$OD) δ 2.48 (s, 3H), 3.88 (s, 2H), 7.81 (s, 1H), 7.85 (s, 1H).

(R)-5-bromo-2,3-dihydro-1H-inden-1-amine

A 22 L 5-necked round-bottomed flask was charged with 5-bromo-1-indanone (1.0 kg, 4.72 mol), anhydrous THF (8 L) and (R)-methyl-CBS-oxazaborolidine (730 mL, 0.73 mol) and was cooled to −10° C. under N$_2$. Borane-methylsulfide (10.0 M, 650 mL, 6.5 mol) was added dropwise over 1 hour while maintaining the temperature below −5° C. The mixture was stirred at −10° C. to 0° C. for 3 hours and was quenched with water (4 L) at such a rate to maintain the reaction temperature below 5° C. The mixture was extracted with EtOAc (3×3 L). The combined organic extracts were washed with brine (2 L), dried over MgSO$_4$, filtered and concentrated to give yellow solid. The crude product was passed through a short silica gel column (3 L silica gel packed with 1% Et$_3$N in hexanes) and eluted with EtOAc/hexanes (1/3). The filtrate was concentrated and the residue was slurried with 10% EtOAc in hexanes, filtered, and dried to give 585 g of an off-white solid as (S)-5-bromo-indan-1-ol. The mother liquors were re-concentrated, slurried with 10% EtOAc in hexanes and filtered to give another 200 g yellow solid as (S)-5-bromo-indan-1-ol. The combined lots (785 g, 78%) were carried on to the next step without further purification.

A solution of (S)-5-bromo-indan-1-ol (288 g, 1.35 mol) in toluene (2 L) was cooled in an ice bath under N$_2$ and treated with diphenylphosphoric azide (DPPA, 400 mL, 1.85 mol) in one portion followed by a solution of 1,8-diazabicyclo[5,4,0] undec-7-ene (300 mL, 2.01 mol) in toluene (600 mL). The reaction temperature was kept between 3 and 10° C. during the 3 hour addition and the mixture was warmed to 15° C. over 3 hours (TLC indicated no starting material). The mixture was diluted with EtOAc (1 L) and washed with water (3×2 L). The organic layer was dried over MgSO$_4$, filtered and concentrated to give 516 g of a dark oil. The crude product was purified by silica gel column (packed with 1% Et$_3$N in hexanes, hexane eluant) to give (R)-1-azido-5-bromo-indane (291 g, 90%) as an oil which was used directly in the next step.

A solution of (R)-1-azido-5-bromo-indane (154 g, 0.645 mol) was dissolved in methanol (2.4 L) and SnCl$_2$.2H$_2$O (265 g, 1.18 mol) was added. The mixture was stirred at room temperature overnight (TLC indicated no starting material) and was concentrated to dryness. The resulting residue was treated with 2N aqueous NaOH (2.5 L) and EtOAc (1.5 L). The mixture was stirred for 1 hour and filtered through Celite® with the aid of EtOAc (3×250 ml). The organic solution was separated and the aqueous layer was extracted with EtOAc (3×2 L). The combined organic extracts were washed with 1 N HCl (2×2 L) followed by water (2 L). The pH of the combined aqueous layers was adjusted to 11 with cold saturated NaOH solution and the mixture was extracted with EtOAc (3×2 L). The combined organic extracts were dried over MgSO$_4$, filtered and concentrated to give (87.5 g, 64.0%) (R)-5-bromo-2,3-dihydro-1H-inden-1-amine as a dark yellow oil which solidified upon refrigeration. MS (ES+) 213.9 (M+H)$^+$. $^1$H NMR (CDCl$_3$) δ 1.70-1.75 (m, 1H), 2.40-2.45 (m, 1H), 2.77-2.82 (m, 1H), 2.93-2.97 (m, 1H), 4.28-4.33 (m, 1H), 7.18-7.23 (m, 1H), 7.36-7.41 (m, 2H).

tert-butyl
4-(chloromethyl)-4-formylpiperidine-1-carboxylate

To a solution of diisopropylamine (22.6 mL, 159 mmol) in anhydrous THF (140 mL) in an oven-dried round-bottomed flask was added n-BuLi (65.4 mL, 163 mmol, 2.50 M in hexanes) dropwise at 0° C. The solution was stirred for 45 minutes and 1-tert-butyl 4-methyl piperidine-1,4-dicarboxylate (20 g, 80 mmol) in THF (60 mL) was added dropwise at 0° C. and the mixture was stirred at 0° C. for 1 hour. Chloroiodomethane (17.9 mL, 239 mmol) was added dropwise and the mixture was stirred for 1 h. The mixture was quenched with 250 mL of saturated aqueous NaHCO$_3$ followed by extraction with ethyl acetate (3×250 mL). The combined organic layers were washed (brine, 250 mL), dried (Na$_2$SO$_4$) and concentrated under reduced pressure to give a yellow oil that was purified by silica chromatography using a Combiflash ISCO purification system (Teledyne Isco Inc., Lincoln, Nebr.) system to give 1-tert-butyl 4-methyl 4-(chloromethyl) piperidine-1,4-dicarboxylate (12 g, 52%). $^1$H NMR (CDCl$_3$) δ 1.43 (s, 9H), 2.10-2.17 (m, 4H), 2.97 (br s, 2H), 3.56 (s, 2H), 3.74 (s, 3H), 3.83 (br s, 2H).

A solution of 1-tert-butyl 4-methyl 4-(chloromethyl)piperidine-1,4-dicarboxylate (11.7 g, 40.2 mmol) in anhydrous THF (100 mL) was cooled to 0° C. Lithium aluminum hydride (1N in THF, 44.3 mL, 44.3 mmol), was added slowly (15-20 min) and the solution was stirred at 0° C. for 25 minutes. The mixture was quenched by adding water (1.8 mL) dropwise with great caution. Aqueous 1N NaOH (1.8 mL) was added dropwise, and the mixture was stirred for 5 minutes. The cooling bath was removed, the solids were filtered off, and the cake was washed with Et$_2$O (2×100 mL). The filtrate was washed with water (2×100 mL), brine (100 mL), dried (Na$_2$SO$_4$) and concentrated under reduced pressure to give tert-butyl 4-(chloromethyl)-4-(hydroxymethyl) piperidine-1-carboxylate as a solid (9.96 g, 93.8%). $^1$H NMR (CDCl$_3$) δ 1.43 (s, 9H), 1.48-1.55 (m, 4H), 3.36-3.41 (m, 4H), 3.57 (s, 2H), 3.59 (br s, 2H).

To a −78° C. solution of oxalyl chloride (5.1 mL, 57 mmol) in dichloromethane (100 mL) in an oven-dried round-bottomed flask was added dimethylsulfoxide (8.2 mL, 114 mmol) in dichloromethane (17 mL). The mixture was stirred for 2 minutes and tert-butyl 4-(chloromethyl)-4-(hydroxymethyl)piperidine-1-carboxylate (13.7 g, 52 mmol) in dichloromethane (50 mL) was added over 10 minutes. The solution was stirred for 15 minutes at −78° C. and triethylamine (36 mL, 260 mmol) was added. The mixture was stirred at −78° C. for 15 minutes and was warmed to room temperature. The mixture was stirred for 15 minutes at room temperature and was quenched with saturated aqueous NaHCO$_3$ (200 mL). The aqueous solution was washed with Et$_2$O (2×300 mL). The combined organic layers were washed with brine, dried (Na$_2$SO$_4$) and concentrated under reduced pressure to give the title compound as a yellow oil that solidified upon standing under nitrogen atmosphere at room temperature (13.7 g, 99%). $^1$H NMR (CDCl$_3$) δ 1.43 (s, 9H), 1.48-1.60 (m, 2H), 2.00-2.07 (m, 2H), 3.07 (t, 2H), 3.57 (s, 2H), 3.69-3.79 (m, 2H), 9.55 (s, 1H).

(R)-tert-butyl 2-(5-bromo-2,3-dihydro-1H-inden-1-yl)-2,7-diazaspiro[3.5]nonane-7-carboxylate To a solution of (R)-5-bromo-2,3-dihydro-1H-inden-1-amine (1835 g, 8.66 mol) in anhydrous methanol (24 L) was added tert-butyl 4-(chloromethyl)-4-formylpiperidine-1-carboxylate (2310 g, 8.83 mol). The mixture was stirred at 50° C. for 16 h, and cooled to rt. Sodium cyanoborohydride (1000 g, 15.9 mol) in THF (15 L) was added via a syringe pump over 2 hours. The mixture was stirred at 60° C. for 24 hours under nitrogen with a vent into a bleach bath. The reaction was cooled to 20° C. and transferred via a cannula into a vessel containing 24 L of 2.5M sodium hydroxide, and 30 L of DCM. The layers were separated and the aqueous layer was extracted with DCM (2×5 L). The aqueous layer was treated to destruct residual sodium cyanoborohydride. The combined organic layers were dried (MgSO$_4$) and concentrated under reduced pressure. The crude material was slurried in MTBE (7 L) by stirring at 40° C. for 1 h and at rt for 1 h. The solid was filtered, and washed with MTBE (2×500 mL) and dried under vacuum oven at 50° C. to give the title product as a white crystals (3657 g, 90%). MS (ES+) 422.3 (M+H)$^+$. $^1$H NMR (CDCl$_3$) δ 1.44 (s, 9H), 1.67 (dd, 4H), 1.84-1.93 (m, 1H), 2.07-2.16 (m, 1H), 2.72-2.81 (m, 1H), 2.95-3.15 (m, 5H), 3.31 (dd, 4H), 3.85 (br s, 1H), 7.12 (d, 1H), 7.28 (br s, 1H), 7.35 (br s, 1H). [α]$_D^{20}$=+39.6 deg (c=1.06 mg/mL, MeOH).

(R)-tert-butyl 2-(5-(6-methylpyrimidin-4-yl)-2,3-dihydro-1H-inden-1-yl)-2,7-diazaspiro[3.5]nonane-7-carboxylate To a 50 mL flask charged with (R)-tert-butyl 2-(5-bromo-2,3-dihydro-1H-inden-1-yl)-2,7-diazaspiro[3.5]nonane-7-carboxylate (4.0 g, 9.49 mmol) was added bis(triphenylphosphine)palladium(II) chloride (0.17 g, 0.24 mmol), potassium acetate (3.73 g, 37.97 mmol), bis(pinacolato)diboron (2.65 g, 10.44 mmol) followed by degassing via vacuum then back-filling with nitrogen 5 times. De-oxygenated (nitrogen stream for 30 minutes prior to addition) toluene (40 mL) was added to the mixture and the reaction was heated at 100° C. for 1.5 hours. The reaction was monitored for completion by HPLC. Upon formation of the boronic ester intermediate, the reaction was cooled to 40° C. and charged with a degassed solution of 4 M sodium hydroxide (11.87 mL, 47.46 mmol) followed by addition of 4-chloro-6-methylpyrimidine (1.53 g, 11.87 mmol). The resulting mixture was then heated to 90° C. for 5 hours under nitrogen. The reaction was cooled to room temperature and charged with water (25 mL). After stirring for 20 minutes, the mixture was filtered to remove black solids. The organic layer was extracted to an aqueous solution containing 1.5 equiv of HCl (40 mL). The organic layer was removed and the resulting solution was treated with (4 g) ISOLUTE® Ultra Pure Si-Thiol silica gel for 1.5 hours and filtered. The aqueous solution was adjusted to pH 7.8 with 4N NaOH and extracted with toluene (40 mL). The toluene layer was concentrated to approximately 15 mL under vacuum at 45° C. and heptane (75 mL) was added slowly and the mixture was stirred at 20° C. for 1 hour. The product was filtered and dried under vacuum at 45° C. for 8 hours to afford the title compound as a white solid (3.56 g, 86%). MS (ES+) 435.5 (M+H)+. $^1$H NMR (CDCl$_3$) δ 1.46 (s, 9H), 1.70-1.74 (m, 4H), 1.90-2.01 (m, 1H), 2.13-2.26 (m, 1H), 2.59 (s, 3H), 2.84-2.93 (m, 1H), 3.04-3.21 (m, 5H), 3.30-3.38 (m, 4H), 3.95-4.02 (m, 1H), 7.40 (d, 1H), 7.56 (s, 1H), 7.87 (d, 1H), 7.95 (s, 1H), 9.12 (s, 1H).

2-[(R)-5-(6-methyl-pyrimidin-4-yl)-indan-1-yl]-2,7-diaza-spiro[3.5]nonane dihydrochloride (R)-tert-butyl 2-(5-(6-methylpyrimidin-4-yl)-2,3-dihydro-1H-inden-1-yl)-2,7-diazaspiro[3.5]nonane-7-carboxylate (72.6 g, 167 mmol) was suspended in methanol (363 mL) and 4M HCl in 1,4-dioxane (251 mL) was added. After stirring for 2 hours, the slurry was concentrated to dryness. The crude material was re-suspended in MeOH (500 mL) and concentrated (3×). The resulting solids were further dried under vacuum at 45° C. to afford the title compound (74.1 g, 99.9%). MS (ES+) 335.2 (M+H)+. $^1$H NMR (CD$_3$OD) δ 2.16-2.23 (m, 5H), 2.59 (br s, 1H), 2.78-2.80 (m, 3H), 3.12 (br s, 1H), 3.19-3.24 (m, 4H), 3.37-3.49 (m, 1H), 4.14-4.23 (m, 3H), 4.49 (br s, 1H), 5.11 (br s, 1H), 7.84 (d, 1H), 8.30-8.34 (m, 2H), 8.46 (s, 1H), 9.36 (s, 1H).

(R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone To a suspension of 2-[(R)-5-(6-methyl-pyrimidin-4-yl)-indan-1-yl]-2,7-diaza-spiro[3.5]nonane dihydrochloride (540 mg, 1.22 mmol) in 10 mL of dichloromethane was added triethylamine (492 mg, 4.90 mmol). Once the mixture became a homogenous solution, it was added to a solution of 2-(2-methylimidazo[2,1-b]thiazol-6-yl)acetic acid hydrochloride (251 mg, 1.28 mmol) in 3 mL of dichloromethane. The mixture was stirred for 5 minutes and HBTU (462 mg, 1.22 mmol) in 2 mL of DMF was added. The reaction was stirred at room temperature for 1.5 hours. The reaction was quenched by the addition of 10 mL of NaHCO$_3$ and was diluted with 50 mL of dichloromethane. The organic layer was washed with saturated brine, dried over Na$_2$SO$_4$, filtered and the filtrate was concentrated. The residue was dissolved in 5 mL of CH$_3$CN and the solution was heated to 100° C. for 1 hour with stirring. The mixture was cooled to room temperature and the resulting solids were vacuum filtered to afford the desired product as an off white powder (428 mg, 69%). MS (ES+) 513.5 (M+H)+. $^1$H NMR (CD$_3$OD) δ 1.70-1.74 (m, 4H), 1.88-1.96 (m, 1H), 2.27-2.34 (m, 2H), 2.40 (s, 3H), 2.58 (s, 3H), 2.86-2.97 (m, 1H), 3.11-3.15 (m, 1H), 3.31-3.34 (m, 3H), 3.52-3.55 (m, 4H), 3.78 (s, 2H), 4.05-4.09 (m, 1H), 7.33 (s, 2H), 7.55 (d, 1H), 7.78-7.79 (m, 1H), 7.94-8.03 (m, 2H), 8.93 (s, 1H). $[α]_D^{20}$=+45.3 deg (c=2.5 mg/mL, MeOH).

In Vitro Assays

Radioligand Binding Assays

To measure the ability of a test compound to bind to the ghrelin receptor, and therefore have the potential to modulate ghrelin activity, radioligand displacement assays were performed. The SPA format was utilized for high throughput screening of test compounds and filter binding served for more comprehensive binding characterization. In both formats test compound affinity is expressed as $K_i$ value, defined as the concentration of compound required to decrease [$^{125}$I] ghrelin binding by 50% for a specific membrane batch at a given concentration of radioligand.

Patient Ghrelin SPA Binding Assay

Ghrelin SPA binding assays were performed in a final volume of 90 μl containing 250 ng patient GHSR1a (HEK293 Tetracycline-Inducible cell line expressing the patient growth secretagogue receptor 1a; prepared as membranes) coupled to 0.5 mg SPA beads (wheat germ agglutinin coated, GE Healthcare, RPNQ0060) and 50 pM [$^{125}$I] ghrelin (Perkin Elmer Life Sciences, NEX-388), plus varying concentrations of test compound or vehicle.

Briefly, assays were prepared at room temperature in 384-well plates (Matrix, 4322) containing 2 μl of test compound in DMSO (or DMSO as vehicle). Assays were initiated by addition of 28 μl assay buffer (50 mM HEPES, 10 mM MgCl$_2$, 0.2% BSA, EDTA-free protease inhibitors—1 tablet/50 ml buffer, pH 7.4), 30 μl 8.3 mg/ml hGHSR1a membrane and 30 μl of 150 pM [$^{125}$I] ghrelin, both in assay buffer.

The mixture was incubated for 8 hours to allow binding to reach equilibrium and the amount of receptor-ligand complex is determined by liquid scintillation counting using a 1450 Microbeta Trilux (Wallac).

Patient Ghrelin Filter Binding Assay

Ghrelin binding assays were performed in a final volume of 100 μl containing 100 ng patient GHSR1a (HEK293 Tetracycline-Inducible cell line expressing the patient growth secretagogue receptor 1a; prepared as membranes) and 50 pM [$^{125}$I] ghrelin (Perkin Elmer Life Sciences, NEX-388), plus varying concentrations of test compound or vehicle.

Briefly, assays were prepared at room temperature in 96-well plates (Costar, 3357) containing 2 μl of test compound in DMSO (or DMSO as vehicle). Assays were initiated by addition of 23 μl assay buffer (50 mM HEPES, 10 mM MgCl$_2$, 0.2% BSA, EDTA-free protease inhibitor tablets—1 tablet/50 ml buffer, pH 7.4), 25 μl 4 mg/ml hGHSR1a membrane and 50 μl of 100 pM [$^{125}$I] ghrelin, both in assay buffer.

The mixture was incubated for 90 minutes at room temperature followed by transfer to a 0.3% PEI-treated, 96-well glass fiber filtration plate (Perkin Elmer, 6005174). The mixture was suctioned dry with vacuum and immediately washed 3 times with 200 μl ice cold 50 mM Tris pH 7.5. Plates were allowed to dry overnight at room temperature and 30 μl Supermix scintillant (Perkin Elmer, 1200-439) is added to each well. The amount of receptor-ligand complex was determined by liquid scintillation counting using a 1450 Microbeta Trilux (Wallac).

Radioligand binding filtration format assays for dog (NM_001099945.1), monkey (XM_001084886.1), mouse (NM_177330), and rat (NM_032075) GHSR1a (all expressed in unique HEK293 Tetracycline-Inducible cell lines) were performed in an identical manner as described for patient GHSR1a except that the final amount of membrane to be used is as follows: 2 μg dog GHSR, 250 ng monkey GHSR, 200 ng mouse GHSR, or 125 ng rat GHSR.

Patient Ghrelin Functional Assay

To measure the ability of a test compound to modulate the activity of patient GHSR1a (agonize, antagonize, partially agonize, inversely agonize), a DELFIA GTP-binding assay (Perkin Elmer, AD0260 and AD0261) was performed. The assay monitors the ligand-dependent exchange of GDP for GTP. GPCR activation results in an increase in fluorescence as receptor-bound GDP is replaced by Europium-labeled GTP. Antagonist binding prevents GDP-GTP exchange whereas binding of an inverse agonist pushes the receptor to the GDP bound (inactive) state, both resulting in decreased fluorescence.

Ghrelin functional assays were performed in a final volume of 39.5 μl containing 720 ng patient GHSR1a (HEK293 Tetracycline-Inducible cell line expressing the patient growth secretagogue receptor 1a, prepared as membranes), 9 nM GTP-Europium and varying concentrations of test compound or vehicle. To test for receptor antagonism, membranes were incubated in the presence of agonist ghrelin (Anaspec, 24158) at the EC$_{80}$ concentration, plus test compound or vehicle.

Briefly, the test compound was prepared at room temperature in 384-well plates (Matrix, 4340). The test compound was first diluted in DMSO then added as 15 μl to 10 μl of basal buffer (50 mM HEPES pH 7.4, 3.7 mM MgCl$_2$, 250 μM EGTA, 125 nM GDP) with and without 9 nM ghrelin peptide. Samples were then transferred as 6 μl to 384-well filter plates (Pall, 5071) containing 30 μl of 24 μg/ml hGHSR1a membrane and 0.35 mg/ml saponin (Perkin Elmer, AD0261) in basal buffer.

The mixture was incubated 24 minutes at room temperature with gentle shaking, followed by the addition of 3.5 μl of 100 nM GTP-Europium in 50 mM HEPES, pH 7.4. Samples were shielded from light and incubated for 90 minutes further at room temperature with gentle shaking. The reactions were suctioned dry with vacuum, washed three times with 75 μl ice cold 1×GTP Wash Solution (Perkin Elmer, AD0261), and immediately read on the Envision 2101 Multilabel Reader (Perkin Elmer) using excitation filter 320 nm and emission filter 615 nm.

Patient Dispersed Islet Cell Assay

Day 1: Patient islet cells in an intravenous (iv) bag are obtained. The islet cells are decanted by attaching a coupler to the iv bag and the liquid is decanted into 50 mL conical tubes. The bag is rinsed with 20 mL of media and pooled. The cells are spun 1 minute at 1000 revolutions per minute (rpm). The cells are then incubated overnight at 37° C., 5% CO$_2$ (10 cm$^2$ suspension dishes, 10 mL media/plate).

Day 2: The islet cells are transferred to a 50 mL conical tube, Hank's Working Buffer without calcium is added and mixed, then the mixture is spun for 1 minute at 1000 rpm. The islets are then washed with Hank's Working Buffer without calcium, mixed and then spun at 1000 rpm for 1 minute. All but 15 mL of buffer is then removed by pipette. 30 μL of 500 mM EDTA [1 mM] is then added and then incubated 8 minutes at room temperature. To this is then added 75 μL of 0.25% Trypsin-EDTA and 15 μl of 2 mg/ml DNAse I [2 μg/ml]. The mixture is incubated for 10 minutes at 30° C. with shaking at 60 rpm. The clot is dispersed by triturating with a 1 mL pipette (50 times). 50 mL of Culture Media is added and passed each over 63 μM nylon membrane. The mixture is spun at 1000 rpm for 1 minute then the media is removed by pipette. Resuspend the pellet and washed cells again with approximately 25 mL Culture Media and spun at 1000 rpm for 1 minute. The supernatant is removed then the pellet is resuspended with approximately 5 mL Culture Media and the cells are counted. "V" bottom plates are seeded with 5000 cells/well (2000/well). The plates are spun at 1000 rpm for 5 minutes and placed in cell culture incubation. 600,000 cells are removed for calcium imaging.

Day 3: Dispersed Islet Assay

The culture media is replaced with 100 μl of incubation buffer containing 3 mM glucose. The plates are spun for 5 minutes at 1000 rpm to re-pellet the islets. Incubate the plates in a 37° C. waterbath continuously gassed with 95% O$_2$/5% CO$_2$ for 45 minutes. Replace the pre-incubation buffer with 50 μl of incubation buffer containing the various test compounds in the appropriate concentration of glucose (n=4 for each sample). The plates are spun for 5 minutes at 1000 rpm to re-pellet the cells. The plates are returned to a waterbath continuously gassed with 95% O$_2$/5% CO$_2$ for 60 minutes. Transfered 40 μl to another plate and assay for insulin using an ELISA Patient Insulin Assay (ALPCO Patient Insulin ELISA; Cat. No. 80-INSHU-E10 available from ALPCO, Salem, N.H., USA).

The pharmacological data provided in Table 1 was obtained for Example 1. The IC50 (5.02 nM) and Ki data (4.37 nM) were obtained from the Patient Ghrelin SPA Binding Assay. The column denoted "n" is the number of times the test compound was assayed. The functionality of the test compound was determined to be inverse agonist using the Patient Ghrelin Functional Assay.

TABLE 1

| In Vitro Assays | Example 1 Pre-incubation | $K_d/K_i$/EC50/IC50 (nM) | $K_i$/EC50/IC50 ng/mL | n |
|---|---|---|---|---|
| Human Binding | | | | |
| Human GHS-1aR SPA | 8 hours | 4.37 | 2.24 | 10 |
| Human GHS-1aR Filter | 90 minutes | 2.49 | 1.28 | 52 |
| Human GHS-1aR Filter | 24 hours | 1.42 | 0.728 | 44 |
| Human GHS-1aR Filter Motulsky | Equilibrium 4.07 hours | 3.04 | 1.56 | 8 |
| Preclinical Species Binding | | | | |
| Rat GHS-1aR Filter | 90 minutes | 3.19 | 1.64 | 49 |
| Mouse GHS-1aR Filter | 90 minutes | 7.70 | 3.95 | 15 |
| Dog GHS-1aR Filter | 90 minutes | 3.56 | 1.83 | 9 |
| Primate GHS-1aR Filter | 90 minutes | 1.83 | 0.938 | 8 |
| Human Functional | | | | |
| Eu-GTP Inverse Agonist | 114 minutes | 4.85 | 2.49 | 16 |
| Eu-GTP Antagonist | 114 minutes | 6.57 | 3.37 | 16 |
| Eu-GTP Competitive Antagonist | 120 minutes | 1.75 | 0.90 | 10 |

GHS-1aR = Growth hormone secretagogue Receptor; Eu-GTP = Europium-guanosine-5'-triphosphate; GH = Growth hormone.

Example 1 is a potent (human $K_d$=3 nM via Patient Ghrelin Filter Binding Assay; similar across species), selective ($IC_{50}$>1 uM against a broad panel of receptors, transporters, ion channels, and enzymes), and moderate on/off inverse agonist, competitive antagonist of the growth hormone secretagogue receptor (GHS-1 aR).

In Vivo Assays

Figure 1:
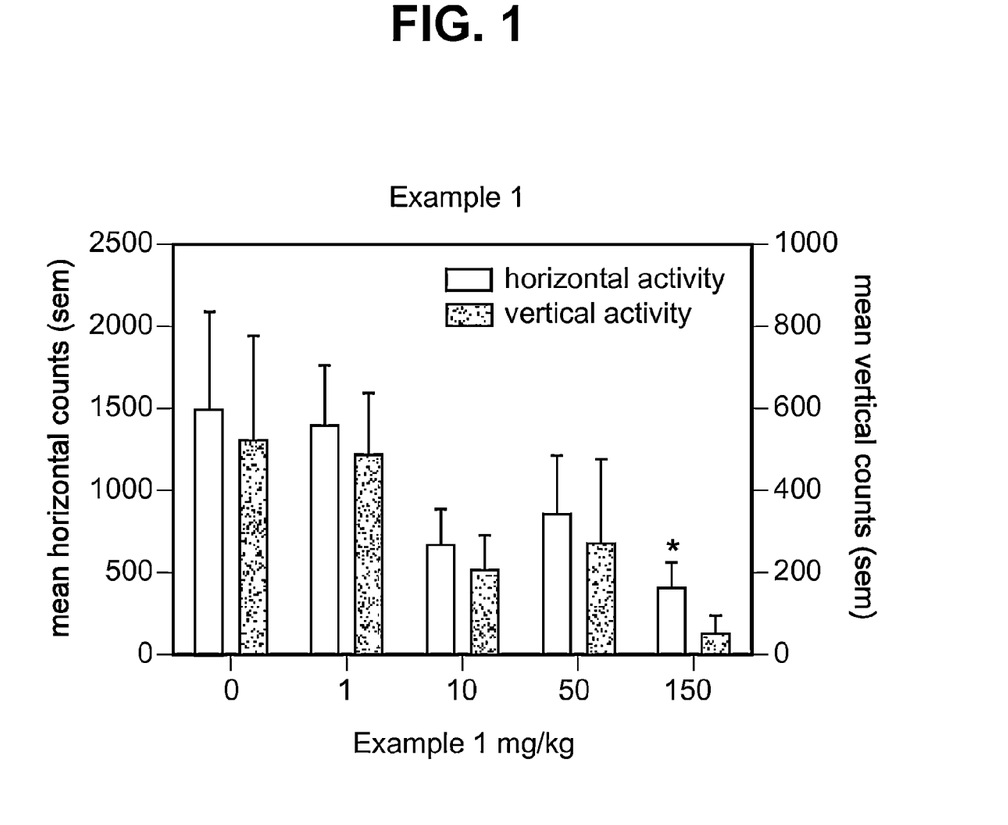
FIG. 1 is a graphical illustration of the effects of Example 1 at reducing locomotor activity in male Wistar Han rats at 35-65 minutes post dosing via oral gavage.

Male Wistar Han rats were administered a single dose (1, 10, 50, or 150 mg/kg) of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone (Example 1) via oral gavage to assess the effects of Example 1 on locomotor activity over a 21 hour period (FIG. 1). Animals were habituated to the locomotor apparatus one hour prior to dosing. The lights were turned off at 4 pm and turned on at 4 am. Animals were dosed at 4 pm. Activity was monitored post-dose for 20 hours. Plasma, brains and CSF were taken from a satellite group of animals at Tmax (30 minutes post dosing).

At 35-65 minutes post dosing, no biologically or statistically significant effect was seen at 1 mg/kg when compared to vehicle treated animals. At 10 mg/kg, Example 1 decreased rearing 56% and total locomotor activity 60% at 35-65 minutes post dosing. At 50 mg/kg, Example 1 decreased rearing 43% and total locomotor activity 48%. Example 1 at 150 mg/kg produced a reduction in total activity which was statistically significant when compared to vehicle control rats (P<0.5) 35-65 minutes post dosing. Example 1 produced no statistically or biologically significant reductions in total activity 20 hours post dosing. Example 1 did not induce hyperactivity at any dose.

The plasma and brain levels of Example 1 were determined at 30 minutes post dosing, shown in Table 2.

TABLE 2

| Dose | Plasma (nM free) | Brain (nM free) |
|---|---|---|
| Vehicle | 0 | 0 |
| 1 mg/kg Ex. 1 | 18 | 1.6 |
| 10 mg/kg Ex. 1 | 184 | 16 |
| 50 mg/kg Ex. 1 | 856 | 80 |
| 150 mg/kg Ex. 1 | 1704 | 148 |

Figure 2:
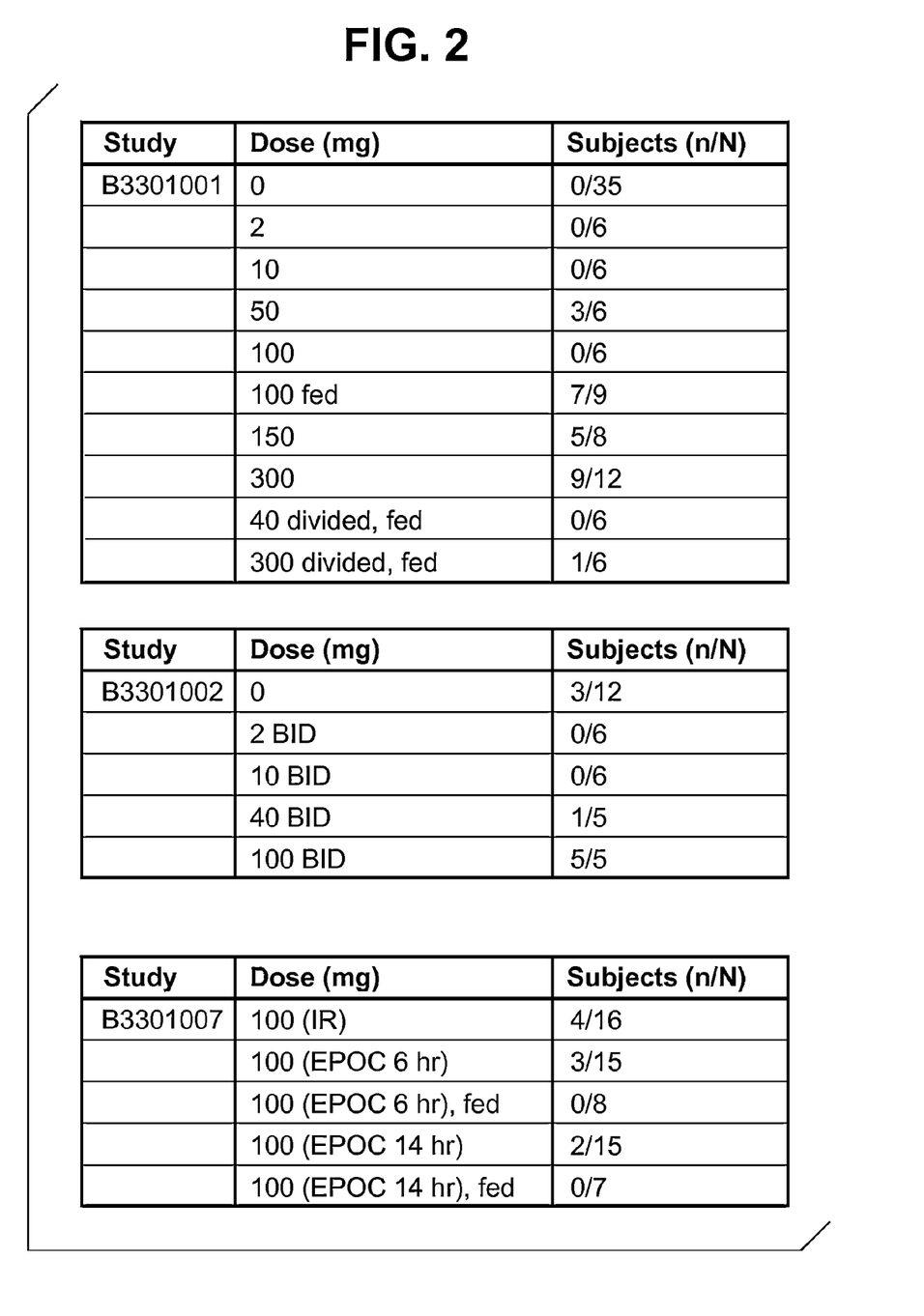
FIG. 2 is a graphical illustration of the somnolence effects of Example 1 in humans.

In three clinical studies (FIG. 2), a dose-responsive relationship was observed with somnolence in humans where, at the highest doses of 100 mg BID for 14 days and 300 mg single doses, between 75 and 100% of subjects reported somnolence or a sleep-related effect. Patients were administered Example 1 as an extemporaneously prepared suspension in B3301001, B3301002, and the IR in B3301007 and as an extemporaneously prepared osmotic capsule (EPOC) in B3301007. Example 1 was safe and generally well tolerated in humans up to 100 mg BID for 14 days which equated to an estimated 80% systemic receptor occupancy for 20 hrs and 70% centrally for approximately 3 hours. Dose related increase in heart rate (up to ~10 beats per minute) as well as attenuation of both ghrelin-induced growth hormone secretion and postprandial glucose were seen after acute dosing. All three of these effects appeared to fully tachyphylax by day 14 of BID dosing.

In a primate study, the effect of Example 1 on sleep duration and food intake three hours post evening dosing Example 1 was studied dosing either once a day (QD) or twice a day (BID). Eight healthy adult (5.8 to 9.7 years of age) male rhesus monkeys, (*Macaca mulatta*, of Indian origin) were used.

Animals were studied in parallel. According to a cross-over design, four of the animals received Example 1 (or Vehicle as a control) QD during the first phase of the study and BID during the second phase of the study. A reverse treatment schedule was used for the remaining four animals. When Example 1 was administered QD, the single dose was administered in the evening. Each treatment period lasted 28-30 consecutive days. Vehicle treatment lasted 10-14 days, immediately preceding the phase where Example 1 was administered. Animals were also kept in their sleep/circadian chambers to become familiar with them. Treatment was administered as a liquid solution, dispensed automatically using a timer-controlled pump.

Throughout treatment periods, animals were maintained in light-controlled and sound attenuated sleep/circadian chambers, under constant conditions of dim light, in order to determine the intrinsic rhythms of sleep/activity and self-administered food intake.

Data Collection:

Sleep/activity cycle and sleep duration was documented using continuous on-line actigraphic image analysis technique, as described in Masuda et al., *J Biol Rhythms*. 2010 October; 25(5):361-71, Intrinsic activity rhythms in *Macaca*

*mulatta*: their entrainment to light and melatonin. A software algorithm for actigraphic data analysis of sleep versus wakefulness in rhesus monkeys is explained in Zhdanova et al., *J Biol Rhythms*. 2011 April; 26(2):149-59. Aging of intrinsic circadian rhythms and sleep in a diurnal nonhuman primate, *Macaca mulatta*. Sleep onset and duration estimates were based on the comparisons between polysomnographic and actigraphic sleep in this species.

Each circadian chamber was equipped with an individual touch-screen monitor, connected to an automatic pellet dispenser (ENV-203-1000, Med Associates Inc., St. Albans, Vt.). This allowed for ad libitum around the clock self-administration of 1 g food pellets (Nutritionally complete dustless precision pellets, Bio-Serv, Frenchtown, N.J.) via pressing a moving on-screen target. The time each pellet dispensed was documented.

Data analysis was conducted using linear mixed model (SPSS), with the level of significance at $p<0.05$. Data were presented as group means (standard error of the means (SEM)) for each treatment condition: QD or BID administration of vehicle or Example 1.

Figure 3:
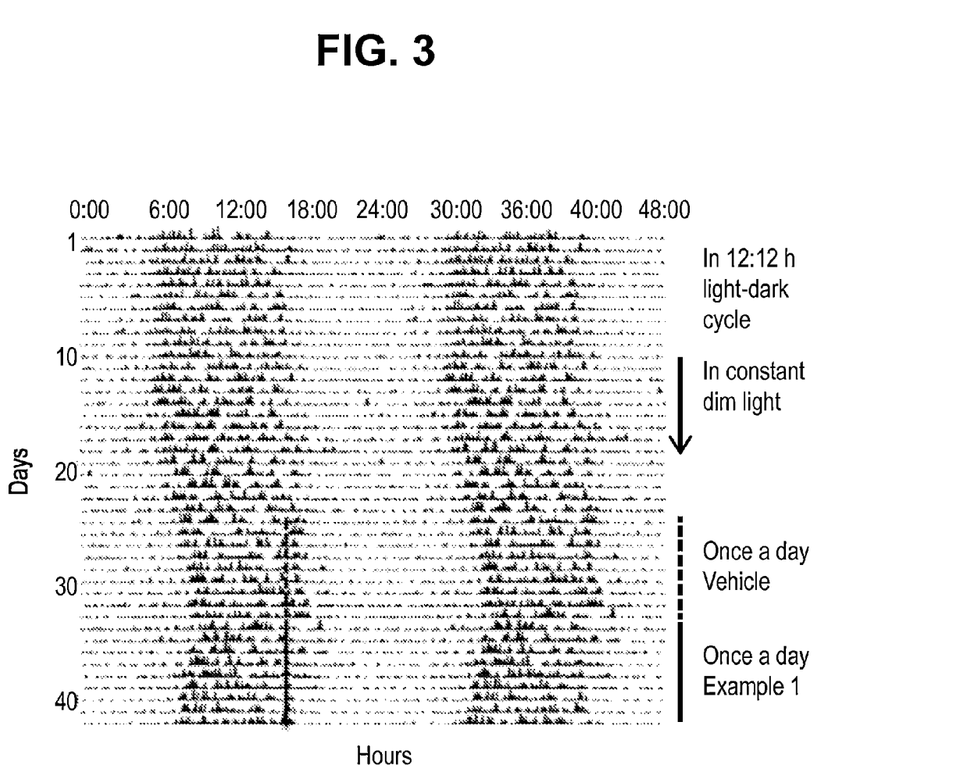
FIG. 3 is an example of an animal's individual activity pattern after once a day (QD) administration of Example 1 or vehicle.
Figure 4:
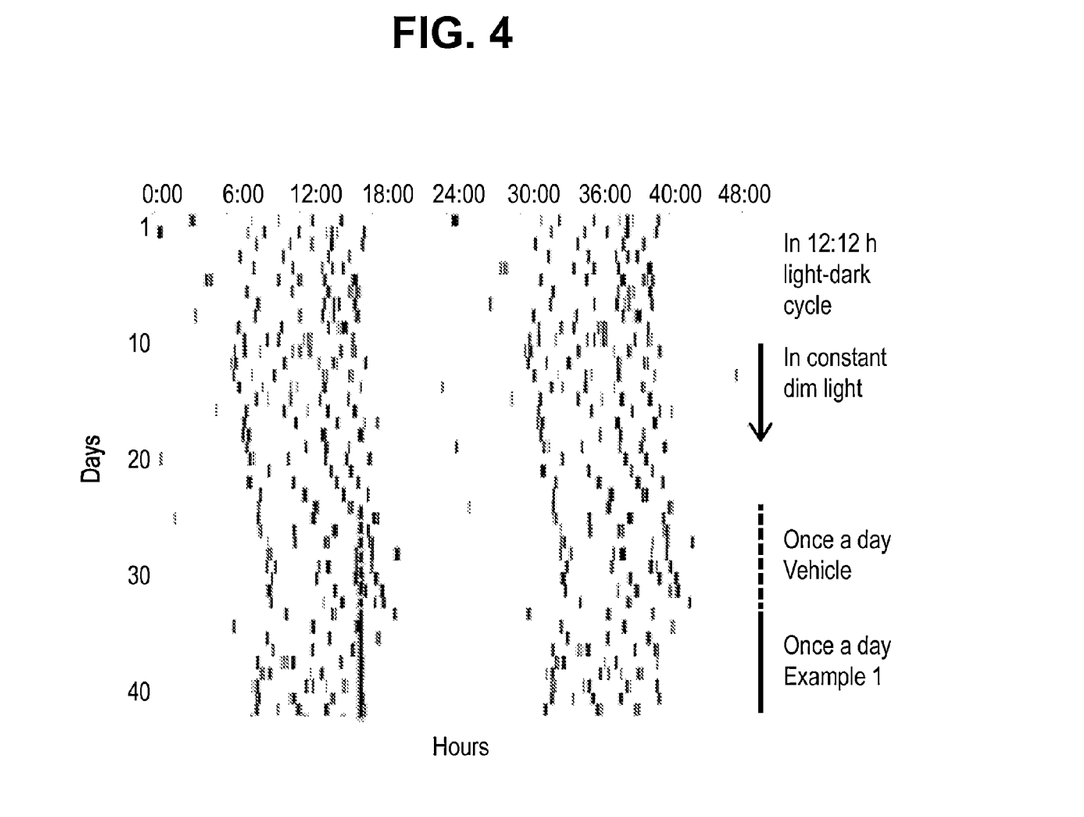
FIG. 4 is an example of an animal's individual food intake pattern after QD administration of Example 1 or vehicle.

FIGS. 3 and 4 provide data on an individual animal's activity pattern (FIG. 3) or food intake pattern (FIG. 4) while receiving evening QD vehicle or Example 1. Actigraphic recordings from animals during a 12:12 hour light-dark cycle (LD) were taken, followed by constant dim light conditions thereafter (arrow along right side of graph). This individual had an intrinsic circadian period longer than 24 hours, illustrated by the entire activity pattern being delayed over time (gradual shift to the right). Vehicle or Example 1 was administered at the same clock time (17:00 hours). At the beginning of the vehicle treatment period (dashed line along right side of graph), this corresponded to a 2-hour prior-to-expected sleep onset (beginning of subjective night). By the time Example 1 treatment was initiated (solid line along right side of graph), this clock time corresponded to around a 3.5 hour prior-to-expected sleep onset.

Treatment with Example 1 significantly reduced sleep latency, facilitating sleep onset, and this effect continued throughout the treatment period. This effect also led to the overall shift of activity pattern to the left (phase advance in wake up time), with earlier sleep onset time resulting in similarly earlier time of awakening on subjective morning.

The Example 1 treatment significantly reduced food intake soon after administration, and this effect continued throughout the treatment period. This effect also led to the overall shift of food intake pattern to the left (phase advance in the time of morning meal). The food intake pattern in this animal followed the activity pattern. Compare FIG. 3 and FIG. 4.

Figure 5:
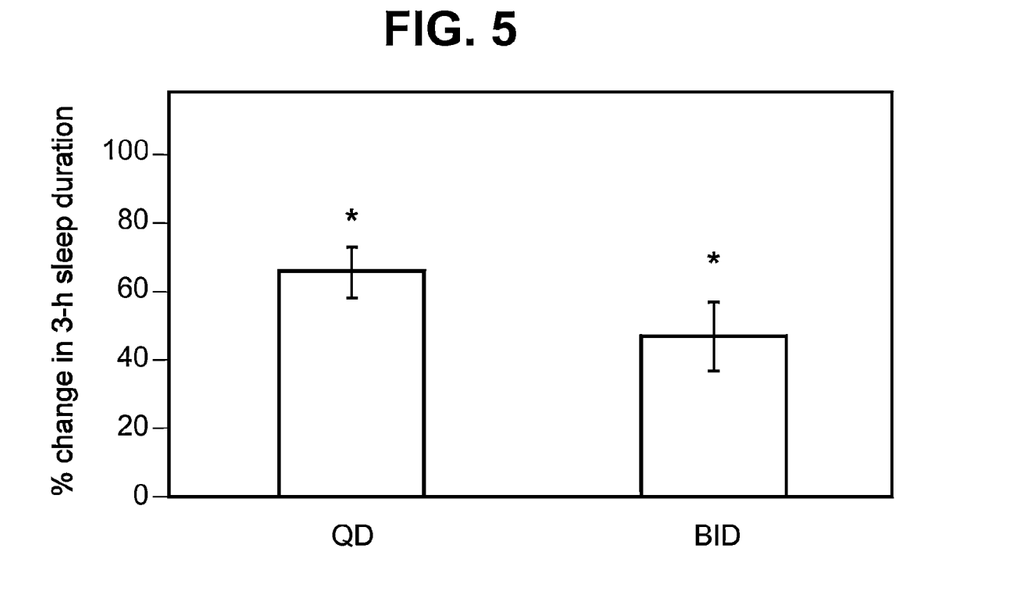
FIG. 5 provides the change in sleep duration within 3 hours following evening administration of Example 1.

FIG. 5 provides the change in sleep duration within 3 hours following evening treatment of Example 1 compared to vehicle (N=8 per group (QD vs BID)). For both groups, a significant increase in sleep duration was documented within 3 hours of treatment of Example 1 compared to administration of just vehicle. The data is expressed as a percent change of sleep duration for when animals receive vehicle compared to the other animals in the group receiving Example 1 (error bars providing the SEM; $p<0.01$ vs. control).

Figure 6:
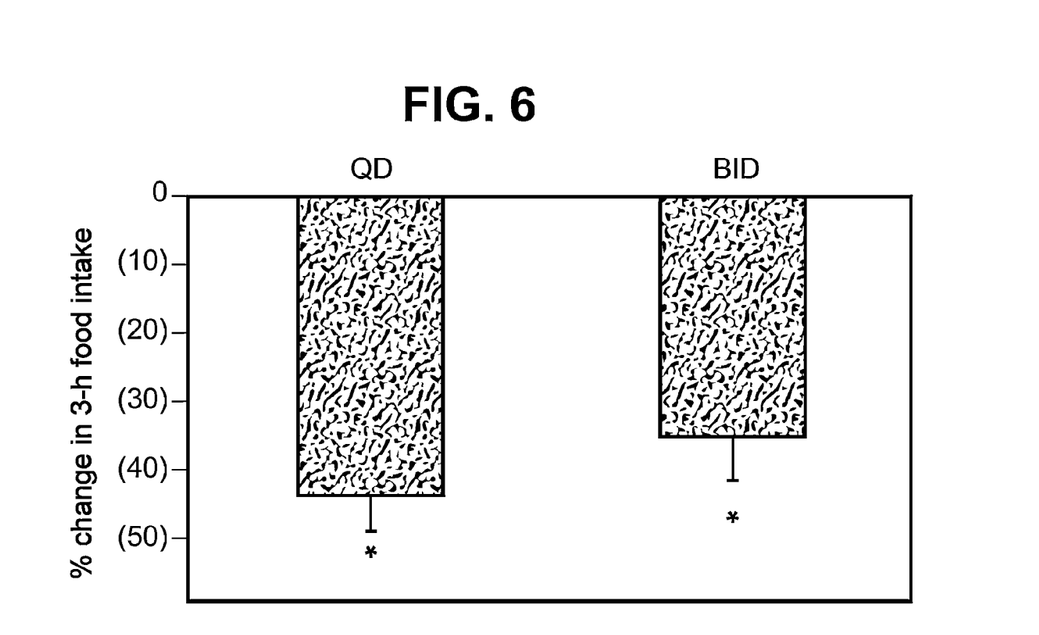
FIG. 6 provides the change in food intake within 3 hours following evening administration of Example 1.

FIG. 6 provides the change in evening food intake within 3 hours following evening administration of Example 1 or vehicle. FIG. 6 provides the change for animals receiving Example 1 QD or BID (N=8 per group (QD vs BID)), for which a significant decrease in food intake was documented for both groups, when compared to administration of just vehicle, within 3 hours of administration of Example 1. The data is expressed as percent of food intake within 3 hours after administration of vehicle or Example 1 (error bars providing the SEM; $p<0.01$ vs. vehicle).

We claim:

1. A method of treating a sleep disorder in a patient comprising the step of administering to the patient, in need of such treatment, a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl)ethanone, or a pharmaceutically acceptable salt thereof, wherein the sleep disorder is primary insomnia.

2. A method of treating a sleep disorder in a patient comprising the step of administering to the patient, in need of such treatment, a pharmaceutical composition comprising a therapeutically effective amount of (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl) ethanone, or a pharmaceutically acceptable salt thereof, and at least one pharmaceutically acceptable carrier, diluent, or excipient, wherein the sleep disorder is primary insomnia.

3. The method of claim 1, wherein (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl) ethanone, or a pharmaceutically acceptable salt thereof is administered in combination with another pharmacologically active agent.

4. The method of claim 2, wherein (R)-2-(2-methylimidazo[2,1-b]thiazol-6-yl)-1-(2-(5-(6-methylpyrimidin-4-yl)-2,3-dihydro-1H-inden-1-yl)-2,7-diazaspiro[3.5]nonan-7-yl) ethanone, or a pharmaceutically acceptable salt thereof is administered in combination with another pharmacologically active agent.

\* \* \* \* \*